(12) United States Patent
Kwak et al.

(10) Patent No.: US 7,896,906 B2
(45) Date of Patent: Mar. 1, 2011

(54) ARTIFICIAL FACET JOINT

(75) Inventors: Seungkyu Daniel Kwak, Grafton, MA (US); John Riley Hawkins, Cumberland, RI (US); Amie Borgstrom, North Attleborough, MA (US); William Dunbar, Norton, MA (US)

(73) Assignee: DePuy Spine, Inc., Raynham, MA (US)

( * ) Notice: Subject to any disclaimer, the term of this patent is extended or adjusted under 35 U.S.C. 154(b) by 1004 days.

(21) Appl. No.: 10/905,374

(22) Filed: Dec. 30, 2004

(65) Prior Publication Data
US 2006/0149229 A1 Jul. 6, 2006

(51) Int. Cl.
*A61B 17/88* (2006.01)
(52) U.S. Cl. ...................... 606/279; 623/17.11
(58) Field of Classification Search .... 623/17.11–17.16; 606/61
See application file for complete search history.

(56) References Cited

U.S. PATENT DOCUMENTS

| | | | |
|---|---|---|---|
| 3,648,691 A | 3/1972 | Lumb et al. | |
| 3,693,616 A | 9/1972 | Roaf et al. | |
| 4,448,191 A | 5/1984 | Rodnyansky et al. | |
| 4,743,260 A | 5/1988 | Burton | |
| 5,084,049 A | 1/1992 | Asher et al. | |
| 5,092,866 A | 3/1992 | Breard | |
| 5,152,303 A | 10/1992 | Allen | |
| 5,176,680 A * | 1/1993 | Vignaud et al. | 606/302 |
| 5,190,543 A * | 3/1993 | Schlapfer | 606/256 |
| 5,261,911 A | 11/1993 | Carl | |
| 5,282,863 A | 2/1994 | Burton | |
| 5,306,275 A | 4/1994 | Bryan | |
| 5,360,429 A * | 11/1994 | Jeanson et al. | 606/61 |
| 5,375,823 A | 12/1994 | Navas et al. | |
| 5,387,213 A | 2/1995 | Breard | |
| 5,403,316 A | 4/1995 | Ashman | |
| 5,415,661 A | 5/1995 | Holmes | |
| 5,425,732 A * | 6/1995 | Ulrich | 606/61 |
| 5,437,669 A * | 8/1995 | Yuan et al. | 606/61 |
| 5,437,671 A | 8/1995 | Lozier et al. | |
| 5,474,086 A | 12/1995 | McCormick et al. | |
| 5,486,174 A * | 1/1996 | Fournet-Fayard et al. | 606/261 |
| 5,496,318 A | 3/1996 | Howland et al. | |
| 5,540,688 A | 7/1996 | Navas | |
| 5,556,431 A | 9/1996 | Buttner-Janz | |
| 5,562,737 A | 10/1996 | Graf | |

(Continued)

FOREIGN PATENT DOCUMENTS

EP 0576379 A1 12/1993

(Continued)

OTHER PUBLICATIONS

EP Search Report, Application No. 05849737.1, Aug. 6, 2009.

*Primary Examiner* — Thomas C Barrett
*Assistant Examiner* — Nicholas Woodall
(74) *Attorney, Agent, or Firm* — Nutter McClennen & Fish LLP

(57) ABSTRACT

Various methods and devices for replacing damaged, injured, diseased, or otherwise unhealthy posterior elements, such as the facet joints, the lamina, the posterior ligaments, and/or other features of a patient's spinal column, are provided. In one exemplary embodiment, the methods and devices are effective to mimic the natural function of the spine by allowing flexion, extension, and lateral bending of the spine, while substantially restricting posterior-anterior shear and rotation of the spine.

9 Claims, 9 Drawing Sheets

U.S. PATENT DOCUMENTS

| | | |
|---|---|---|
| 5,571,191 A | 11/1996 | Fitz |
| 5,591,165 A | 1/1997 | Jackson |
| 5,601,554 A | 2/1997 | Howland et al. |
| 5,672,175 A * | 9/1997 | Martin .................. 606/86 A |
| 5,681,312 A | 10/1997 | Yuan et al. |
| 5,716,355 A | 2/1998 | Jackson |
| 5,725,582 A | 3/1998 | Bevan et al. |
| 5,733,284 A | 3/1998 | Martin et al. |
| 5,755,796 A * | 5/1998 | Ibo et al. .................. 623/17.16 |
| 5,766,254 A | 6/1998 | Gelbard |
| 5,810,815 A | 9/1998 | Morales et al. |
| RE36,221 E | 6/1999 | Breard |
| 5,928,233 A * | 7/1999 | Apfelbaum et al. ........... 606/61 |
| 5,938,663 A | 8/1999 | Petreto |
| 5,961,516 A | 10/1999 | Graf |
| 6,019,760 A * | 2/2000 | Metz-Stavenhagen et al. 606/61 |
| RE36,758 E | 6/2000 | Fitz |
| 6,132,464 A | 10/2000 | Martin |
| 6,241,730 B1 * | 6/2001 | Alby ........................ 606/256 |
| 6,248,106 B1 | 6/2001 | Ferree |
| 6,267,764 B1 | 7/2001 | Elberg |
| 6,273,888 B1 | 8/2001 | Justis |
| 6,355,038 B1 | 3/2002 | Pisharodi |
| 6,364,883 B1 | 4/2002 | Santilli |
| 6,419,703 B1 | 7/2002 | Fallin |
| 6,440,169 B1 | 8/2002 | Elberg et al. |
| 6,468,276 B1 | 10/2002 | McKay |
| 6,547,790 B2 | 4/2003 | Harkey |
| 6,551,322 B1 | 4/2003 | Lieberman |
| 6,551,332 B1 | 4/2003 | Nguyen et al. |
| 6,554,831 B1 | 4/2003 | Rivard |
| 6,554,832 B2 | 4/2003 | Shluzas |
| 6,565,605 B2 | 5/2003 | Goble |
| 6,579,319 B2 | 6/2003 | Goble |
| 6,610,091 B1 | 8/2003 | Reiley |
| 6,626,904 B1 | 9/2003 | Jammet et al. |
| 6,626,909 B2 | 9/2003 | Chin |
| 6,626,944 B1 | 9/2003 | Taylor |
| 6,645,207 B2 | 11/2003 | Dixon |
| 6,669,729 B2 | 12/2003 | Chin |
| 6,811,567 B2 | 11/2004 | Reiley |
| 7,011,685 B2 | 3/2006 | Arnin et al. |
| 7,074,237 B2 | 7/2006 | Goble et al. |
| 7,104,992 B2 * | 9/2006 | Bailey ........................ 606/278 |
| 7,189,236 B2 * | 3/2007 | Taylor et al. .................. 606/277 |
| 7,270,665 B2 * | 9/2007 | Morrison et al. ............ 606/300 |
| 2002/0029039 A1 | 3/2002 | Zucherman et al. |
| 2002/0055740 A1 | 5/2002 | Lieberman |
| 2002/0065557 A1 | 5/2002 | Goble |
| 2002/0072800 A1 | 6/2002 | Goble |
| 2002/0123806 A1 | 9/2002 | Reiley |
| 2002/0133155 A1 | 9/2002 | Ferree |
| 2002/0151978 A1 * | 10/2002 | Zacouto et al. ............ 623/17.12 |
| 2003/0004572 A1 | 1/2003 | Goble |
| 2003/0028250 A1 | 2/2003 | Reiley |
| 2003/0055427 A1 | 3/2003 | Graf |
| 2003/0083657 A1 | 5/2003 | Drewry |
| 2003/0093078 A1 | 5/2003 | Ritland |
| 2003/0109880 A1 | 6/2003 | Shirado |
| 2003/0135277 A1 | 7/2003 | Bryan et al. |
| 2003/0153912 A1 | 8/2003 | Graf |
| 2003/0171749 A1 | 9/2003 | Le Couedic |
| 2003/0171750 A1 | 9/2003 | Chin |
| 2003/0176926 A1 | 9/2003 | Boehm et al. |
| 2003/0187438 A1 * | 10/2003 | Assaker et al. .................. 606/61 |
| 2003/0187454 A1 | 10/2003 | Gill et al. |
| 2003/0191470 A1 | 10/2003 | Ritland |
| 2003/0191532 A1 | 10/2003 | Goble |
| 2003/0220642 A1 | 11/2003 | Freudiger |
| 2003/0220643 A1 | 11/2003 | Ferree |
| 2004/0002708 A1 | 1/2004 | Ritland |
| 2004/0006391 A1 | 1/2004 | Reiley |
| 2004/0015174 A1 | 1/2004 | Null et al. |
| 2004/0049189 A1 | 3/2004 | Le Couedic |
| 2004/0049190 A1 * | 3/2004 | Biedermann et al. ........... 606/61 |
| 2004/0049272 A1 | 3/2004 | Reiley |
| 2004/0049273 A1 | 3/2004 | Reiley |
| 2004/0049274 A1 | 3/2004 | Reiley |
| 2004/0049275 A1 | 3/2004 | Reiley |
| 2004/0049276 A1 | 3/2004 | Reiley |
| 2004/0049277 A1 | 3/2004 | Reiley |
| 2004/0049278 A1 | 3/2004 | Reiley |
| 2004/0049281 A1 | 3/2004 | Reiley |
| 2004/0073215 A1 | 4/2004 | Carli |
| 2004/0097950 A1 | 5/2004 | Foley et al. |
| 2004/0111154 A1 | 6/2004 | Reiley |
| 2004/0116927 A1 | 6/2004 | Graf |
| 2004/0127989 A1 | 7/2004 | Dooris et al. |
| 2004/0133203 A1 | 7/2004 | Young et al. |
| 2004/0138660 A1 | 7/2004 | Serhan |
| 2004/0143264 A1 | 7/2004 | McAfee |
| 2004/0147928 A1 * | 7/2004 | Landry et al. .................. 606/61 |
| 2004/0186475 A1 | 9/2004 | Falahee |
| 2004/0186575 A1 | 9/2004 | Varga et al. |
| 2004/0236329 A1 | 11/2004 | Panjabi |
| 2004/0249379 A1 | 12/2004 | Winslow et al. |
| 2004/0267259 A1 | 12/2004 | Mazda et al. |
| 2005/0033431 A1 | 2/2005 | Gordon et al. |
| 2005/0033432 A1 | 2/2005 | Gordon et al. |
| 2005/0033434 A1 | 2/2005 | Berry |
| 2005/0033439 A1 | 2/2005 | Gordon et al. |
| 2005/0049708 A1 | 3/2005 | Atkinson et al. |
| 2005/0055096 A1 | 3/2005 | Serhan et al. |
| 2005/0101954 A1 | 5/2005 | Simonson |
| 2005/0101956 A1 | 5/2005 | Simonson |
| 2005/0113927 A1 | 5/2005 | Malek |
| 2005/0119748 A1 | 6/2005 | Reiley et al. |
| 2005/0131409 A1 | 6/2005 | Chervitz et al. |
| 2005/0171610 A1 * | 8/2005 | Humphreys et al. ........ 623/17.15 |
| 2005/0203518 A1 | 9/2005 | Biedermann et al. |
| 2005/0228381 A1 * | 10/2005 | Kirschman ..................... 606/61 |
| 2005/0228501 A1 * | 10/2005 | Miller et al. ............... 623/17.14 |
| 2005/0240265 A1 * | 10/2005 | Kuiper et al. .............. 623/17.11 |
| 2005/0245929 A1 | 11/2005 | Winslow et al. |
| 2005/0256578 A1 | 11/2005 | Blatt et al. |
| 2005/0277922 A1 | 12/2005 | Trieu et al. |
| 2005/0277930 A1 | 12/2005 | Parsons |
| 2006/0036240 A1 | 2/2006 | Colleran et al. |
| 2006/0052785 A1 | 3/2006 | Augostino et al. |
| 2006/0079896 A1 | 4/2006 | Kwak et al. |
| 2006/0084976 A1 | 4/2006 | Borgstrom et al. |
| 2006/0084984 A1 | 4/2006 | Kim |
| 2006/0084991 A1 | 4/2006 | Borgstrom et al. |
| 2006/0129239 A1 | 6/2006 | Kwak |
| 2006/0149229 A1 | 7/2006 | Kwak et al. |
| 2006/0149230 A1 | 7/2006 | Kwak et al. |
| 2006/0189983 A1 | 8/2006 | Fallin et al. |
| 2006/0200130 A1 | 9/2006 | Hawkins et al. |
| 2006/0241771 A1 * | 10/2006 | Gordon et al. ............. 623/17.15 |
| 2006/0265074 A1 * | 11/2006 | Krishna et al. ............. 623/17.15 |
| 2006/0271046 A1 | 11/2006 | Kwak et al. |

FOREIGN PATENT DOCUMENTS

| | | |
|---|---|---|
| EP | 0669109 | 2/1994 |
| EP | 0612507 A1 | 8/1994 |
| EP | 1153577 | 11/2001 |
| FR | 2694182 A | 2/1994 |
| FR | 2697428 A1 | 5/1994 |
| FR | 2701833 A1 | 9/1994 |
| WO | WO-01/45576 | 6/2001 |
| WO | WO-02/17803 | 3/2002 |
| WO | WO-02/43603 | 6/2002 |
| WO | WO-02/102259 | 12/2002 |
| WO | WO-03/007828 | 1/2003 |
| WO | WO-03/009737 | 2/2003 |
| WO | 2004024011 A1 | 3/2004 |
| WO | WO-2004/034916 | 4/2004 |

* cited by examiner

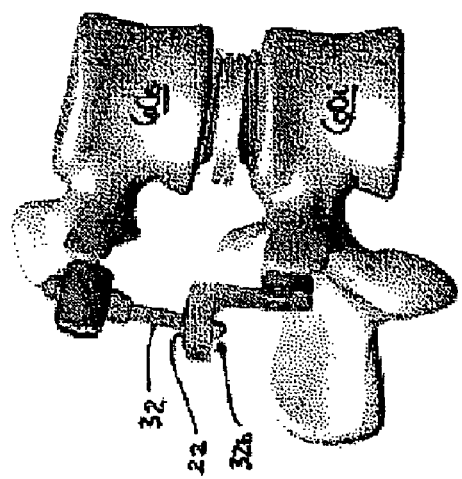
FIG. 4C  Flexion
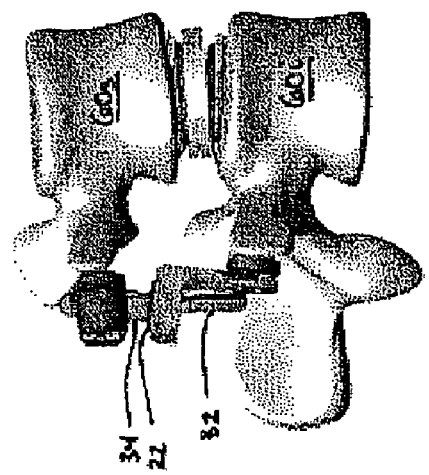
FIG. 4B  Extension
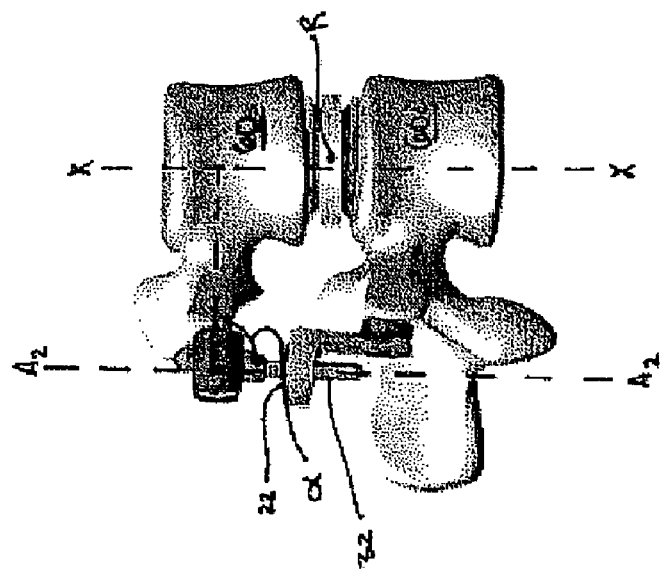
FIG. 4A  Neutral

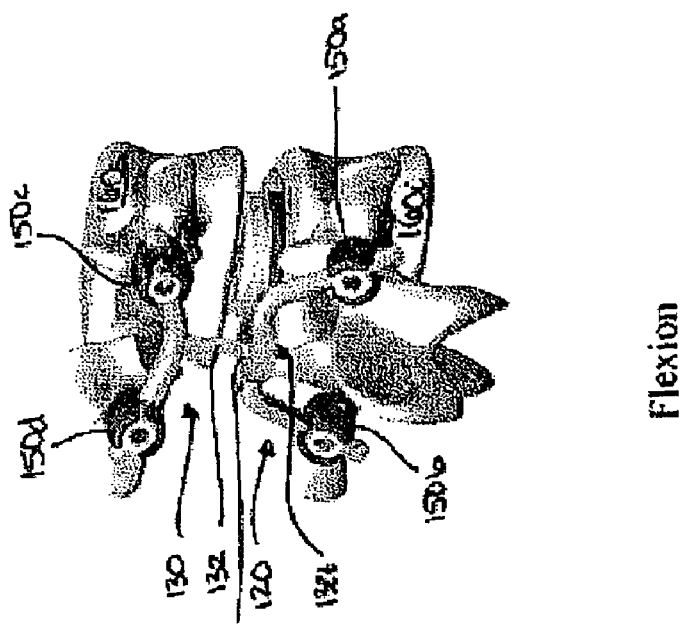
FIG. 8C  Flexion
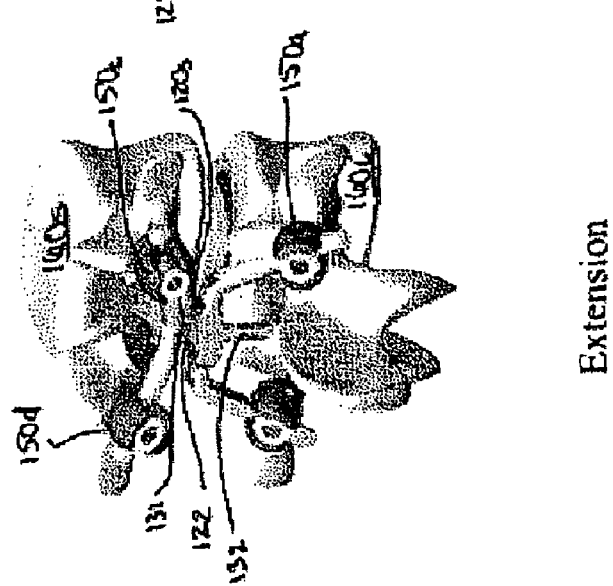
FIG. 8B  Extension
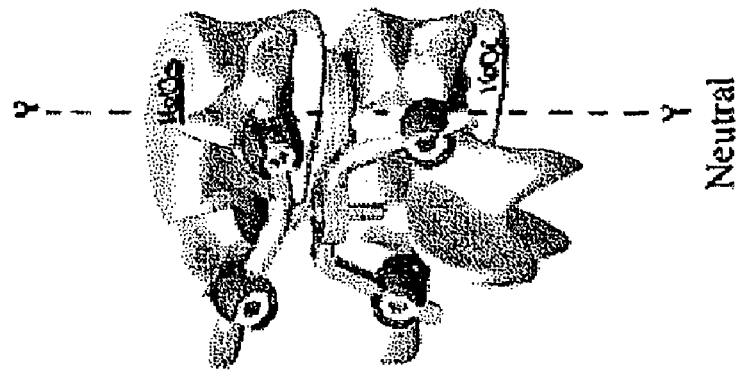
FIG. 8A  Neutral

ARTIFICIAL FACET JOINT

FIELD OF THE INVENTION

The present invention relates to spinal instrumentation, and in particular to various devices that are adapted to mimic the natural function of the structural posterior elements.

BACKGROUND OF THE INVENTION

The vertebrae in a patient's spinal column are linked to one another by the disc and the facet joints, which control movement of the vertebrae relative to one another. Each vertebra has a pair of articulating surfaces located on the left side, and a pair of articulating surfaces located on the right side, and each pair includes a superior articular surface, which faces upward, and an inferior articular surface, which faces downward. Together the superior and inferior articular surfaces of adjacent vertebra form a facet joint. Facet joints are synovial joints, which means that each joint is surrounded by a capsule of connective tissue and produces a fluid to nourish and lubricate the joint. The joint surfaces are coated with cartilage allowing the joints to move or articulate relative to one another.

Diseased, degenerated, impaired, or otherwise painful facet joints and/or discs can require surgery to restore function to the three joint complex. Subsequent surgery may also be required after a laminectomy, as a laminectomy predisposes the patient to instability and may lead to post-laminectomy kyphosis (abnormal forward curvature of the spine), pain, and neurological dysfunction. Damaged, diseased levels in the spine were traditionally fused to one another. While such a technique may relieve pain, it effectively prevents motion between at least two vertebrae. As a result, additional stress may be applied to the adjoining levels, thereby potentially leading to further damage.

More recently, techniques have been developed to restore normal function to the facet joints. One such technique involves covering the facet joint with a cap to preserve the bony and articular structure. Capping techniques, however, are limited in use as they will not remove the source of the pain in osteoarthritic joints. Caps are also disadvantageous as they must be available in a variety of sizes and shapes to accommodate the wide variability in the anatomical morphology of the facets. Caps also have a tendency to loosen over time, potentially resulting in additional damage to the joint and/or the bone support structure containing the cap.

Other techniques for restoring the normal function to the posterior element involve arch replacement, in which superior and inferior prosthetic arches are implanted to extend across the vertebra. The arches may have rigid surfaces that can articulate relative to one another to replace the articulating function of the facet joints. However, aligning two articulating rigid surfaces for facet replacements can be very difficult given the variations in patient anatomy and various motion required (i.e., flexion, extension, lateral bending, and translations).

Accordingly, there remains a need for improved systems and methods that are adapted to mimic the natural function of the facet joints.

BRIEF SUMMARY OF THE INVENTION

The present invention provides various methods and devices for repairing and/or replacing a damaged facet joint, and optionally for replacing other posterior elements, including, for example, the lamina, the posterior ligaments, and/or other features of a patient's spinal column. In one exemplary embodiment, an implantable device for replacing and/or stabilizing one or more facet joints in a patient's spinal column is provided and it generally includes a first member that is adapted to couple to a first vertebra and having a bearing element rotatably disposed therein with an opening formed therethrough, and a second member that is adapted to couple to a second vertebra adjacent to the first vertebra. The second member can include an extension rod that is adapted to extend through the opening formed in the bearing element to control movement between the first and second vertebrae.

While the first and second members can have a variety of configurations, in one exemplary embodiment the first member can be substantially U-shaped with opposed arms extending from a central portion, and the second member can be substantially Y-shaped with opposed arms extending from a terminal end of the extension rod. In use, each arm on the first and second members can be adapted to be received within a receiving head of a bone engaging element, such as a bone screw, to attach each arm to a vertebra. The device can also include at least one compressive element positioned between the central portion of the first member and the central portion of the second member, and at least one compressive element positioned between the central portion of the second member and a terminal end of the extension rod. The compressive element(s) can be adapted to facilitate controlled movement of the adjacent vertebrae.

The bearing element can also have a variety of configurations, but in one exemplary embodiment the bearing element can be a ball bearing having an opening formed therethrough. The opening formed through the bearing element can include a coating formed thereon that is adapted to reduce friction between the bearing element and the extension rod. The bearing element can also be disposed at various locations on the first member, but in one exemplary embodiment the bearing element can be freely rotatably disposed within the central portion of the first member. In particular, the central portion can include a substantially spherical opening formed therein for rotatably seating the bearing element.

In another embodiment of the invention, the extension rod can include at least one stop member formed thereon and adapted to limit slidable movement of the extension rod relative to the bearing element. For example, the extension rod can include first and second stop members formed on first and second terminal ends thereof. The stop member(s) can have a variety of configurations, and it can be formed from a variety of materials including, for example, a compressive material. In one embodiment, the stop member(s) can be in the form of a ring-shaped member that is disposed around the extension rod. An exemplary ring-shaped member has a diameter that is greater than a diameter of the opening in the bearing element.

In yet another embodiment, the first member can be substantially L-shaped with a first portion that is adapted to mate to a bone engaging element, and a second portion having the bearing element rotatably disposed therein. The first portion of the first member can include an opening formed therein for receiving a portion of a locking mechanism adapted to couple the first portion of the first member to a bone engaging element. The first portion of the first member can also include an articulating surface formed thereon and that is adapted to be received within a complementary surface formed on a bone engaging element. In one exemplary embodiment, the articulating surface can be substantially spherical.

In another exemplary embodiment, the second member can be a substantially elongate member having a first portion that is adapted to mate to a bone engaging element and a second portion that is adapted to be disposed through the bearing element. The first and second portions of the second member can be axially offset from one another. The second member can also include a stop formed thereon between the first and second portions. The stop can be adapted to limit movement of the second portion relative to the bearing.

One exemplary method for stabilizing the posterior element in adjacent vertebrae is also provided. The method can include coupling a first member to a first vertebra and a second member to a second vertebra such that an extension rod on the first member extends through a bearing element rotatably disposed within the second member to control movement of the first and second vertebrae relative to one another. The method can also include positioning the extension rod at a predetermined angle relative to a central axis of the first and second vertebrae.

In one exemplary embodiment, the first member can be coupled to the first vertebra by implanting first and second bone engaging members in the first vertebra and mating a portion of the first member to the first and second bone engaging members, and the second member can be coupled to the second vertebra by implanting first and second bone engaging members in the second vertebra and mating a portion of the second member to the first and second bone engaging members. The first and second bone engaging members can be implanted an opposed lateral sides of each vertebra.

In another exemplary embodiment, the first member can be coupled to the first vertebra by implanting a bone engaging member in the first vertebra and mating a portion of the first member to the bone engaging member, and the second member can be coupled to the second vertebra by implanting a bone engaging member in the second vertebra and mating a portion of the second member to the bone engaging member.

BRIEF DESCRIPTION OF THE DRAWINGS

The invention will be more fully understood from the following detailed description taken in conjunction with the accompanying drawings, in which:

FIG. 4A is a side view of one of the posterior stabilizing implants shown in FIG. 1A showing the adjacent vertebrae in a neutral position;

FIG. 4B is a side view of one of the posterior stabilizing implants shown in FIG. 1A showing extension of the adjacent vertebrae;

FIG. 4C is a side view of one of the posterior stabilizing implants shown in FIG. 1A showing flexion of the adjacent vertebrae

FIG. 8A is a side view of the posterior stabilizing implant shown in FIG. 5A showing the adjacent vertebrae in a neutral position;

FIG. 8B is a side view of the posterior stabilizing implant shown in FIG. 5A showing extension of the adjacent vertebrae; and FIG. 8C is a side view of the posterior stabilizing implant shown in FIG. 5A showing flexion of the adjacent vertebrae.

DETAILED DESCRIPTION OF THE INVENTION

The present invention provides various methods and devices for replacing damaged, injured, diseased, or otherwise unhealthy posterior elements, such as the facet joints, the lamina, the posterior ligaments, and/or other features of a patient's spinal column. In one exemplary embodiment, the methods and devices are effective to mimic the natural function of the spine by allowing flexion, extension, and lateral bending of the spine, while substantially restricting posterior-anterior shear and rotation of the spine. A person skilled in the art will appreciate that, while the methods and devices are especially configured for use in restoring and/or replacing the facet joints and optionally other posterior elements of a patient's spine, the methods and devices can be used for a variety of other purposes in a variety of other surgical procedures.

Figure 1A:
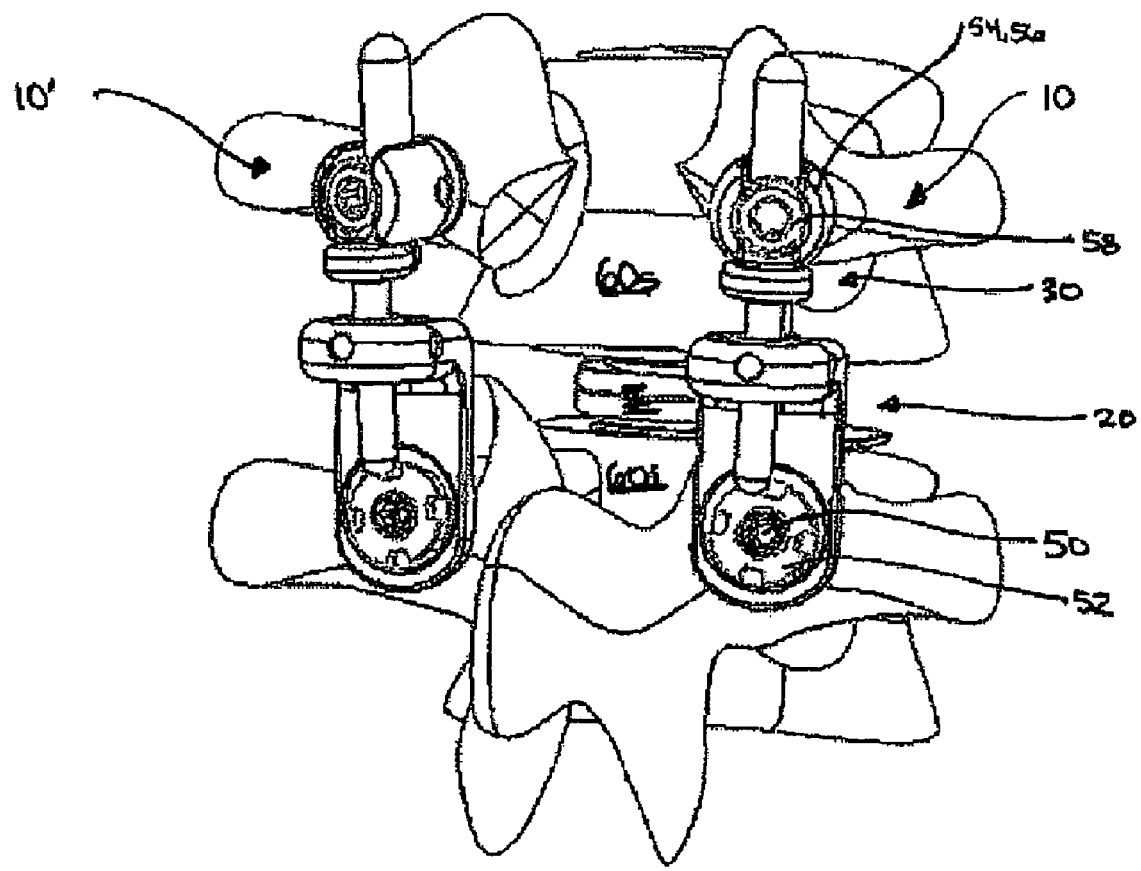
FIG. 1A is perspective view of two exemplary posterior stabilizing implants coupled to adjacent vertebrae.

FIGS. 1A-4C illustrate one exemplary embodiment of a posterior stabilizing implant. While two implants 10, 10' are shown coupled to opposed lateral sides of two adjacent vertebrae 60s, 60i, only one implant 10 will be discussed herein. A person skilled in the art will understand that the implants 10, 10' can have substantially the same configuration. Moreover, while only two implants 10, 10' are shown, additional implants can be coupled to additional vertebrae located along the patient's spinal column. FIGS. 1A-1B also illustrate an artificial disc/implanted between the adjacent vertebrae 60s, 60i. A person skilled in the art will appreciate that the posterior stabilizing implants disclosed herein can be used with a natural disc or with an artificial disc. In an exemplary embodiment, where an artificial disc is used, the disc is preferably one which allows movement of the adjacent vertebrae 60s, 60i relative to one another. By way of non-limiting example, one exemplary artificial disc for use with the present invention is the Charité™ Artificial Disc available from DePuy Spine, Inc.

Figure 1B:
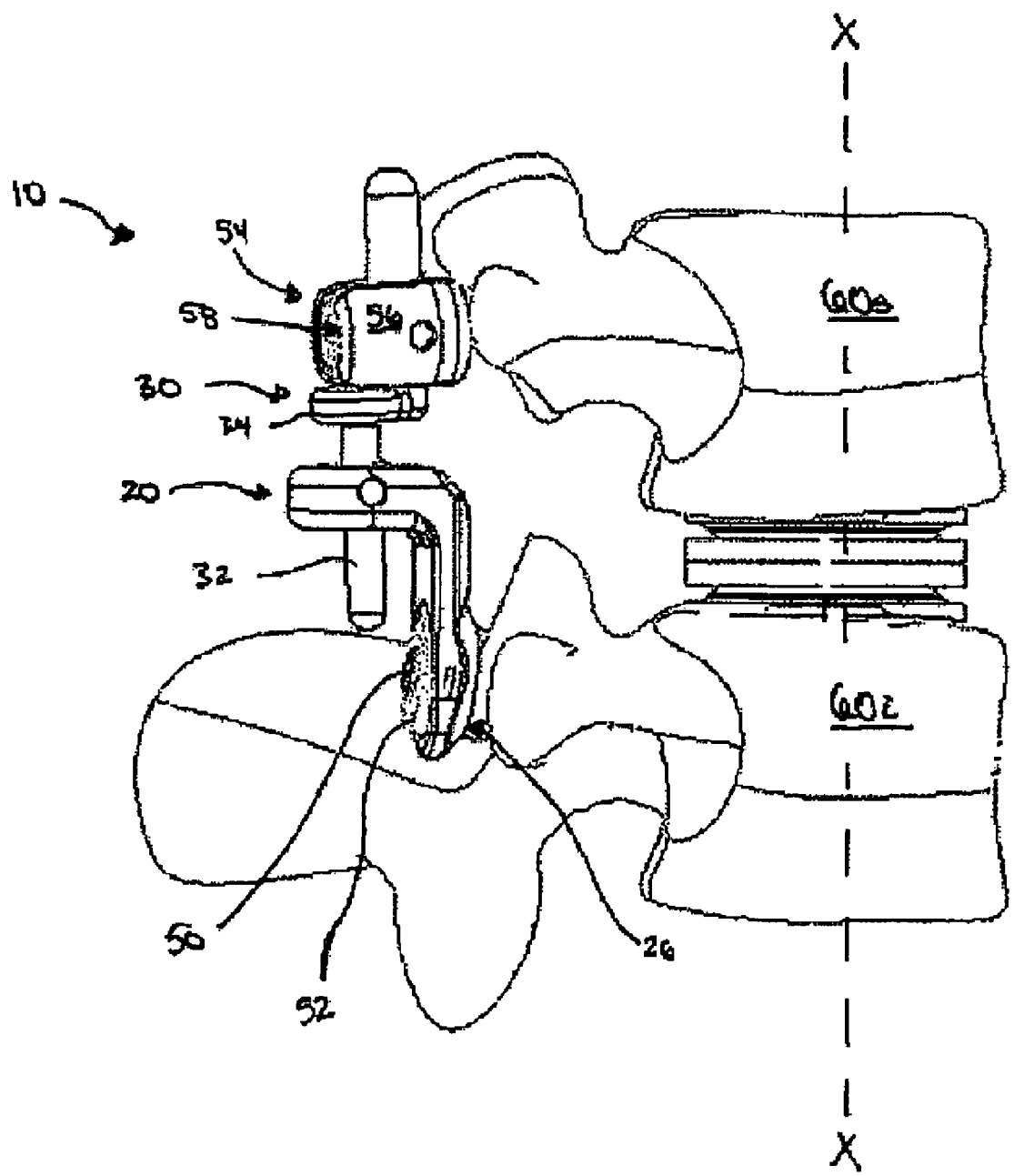
FIG. 1B is a side view of one of the posterior stabilizing implants shown in FIG. 1A coupled to adjacent vertebrae.

As shown in FIGS. 1A-1B, the implant 10 can include a first member 20 that is coupled to a first vertebra, e.g., the inferior vertebra 60i, and a second member 30 that is coupled to a second vertebra, e.g., the superior vertebra 60s. While not shown, the first and second members 20, 30 can be reversed such that the first member 20 is coupled to the superior vertebra 60s and the second member 30 is coupled to the inferior vertebra 60i. The first and second members 20, 30 can also be movably coupled to one another. In particular, the first member 20 can include a bearing element 22 movably disposed therein, and the second member 30 can include an extension rod 32 that is adapted to slidably extend through the bearing element 22. In use, the bearing element 22 and the extension rod 32 cooperate to control movement of the superior and inferior vertebrae 60s, 60i relative to one another, and in particular they allow flexion, extension, and lateral bending of the vertebrae 60s, 60i, while substantially restricting posterior-anterior shear and rotation of the vertebrae 60s, 60i.

Figure 2B:
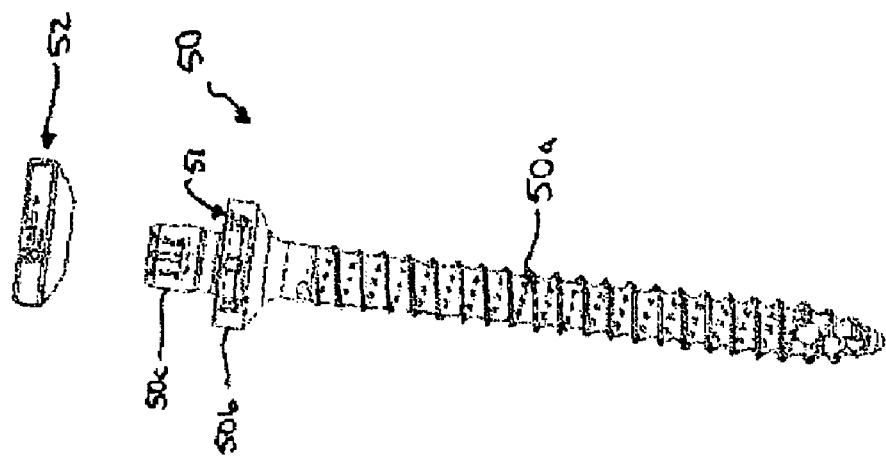
FIG. 2B is a perspective view of one exemplary embodiment of a bone screw and a locking mechanism for use with the first member shown in FIG. 2A.
Figure 2A:
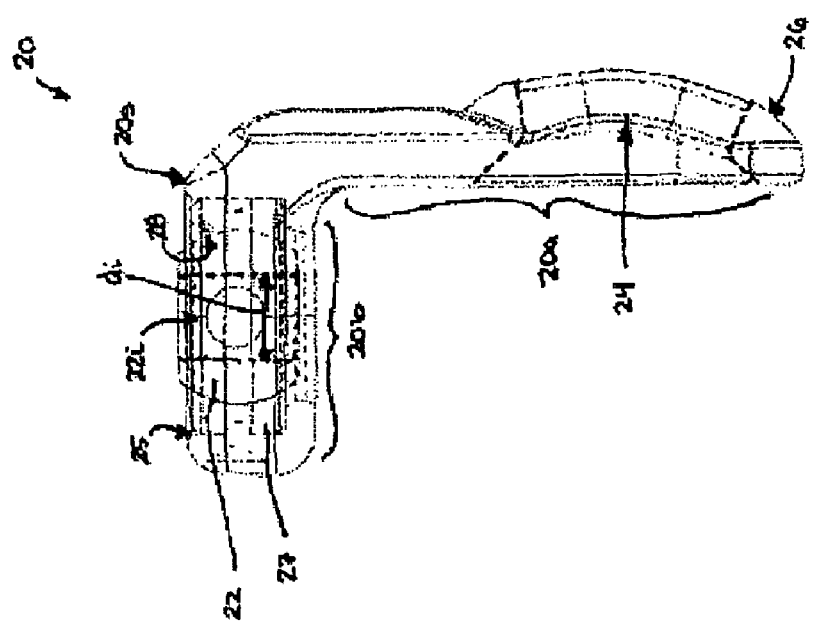
FIG. 2A is a side view of a first member of one of the exemplary implants shown in FIG. 1A.

The first member 20 of the implant 10, which is shown in more detail in FIG. 2A, can have a variety of configurations. In the illustrated exemplary embodiment, however, the first member 20 is substantially L-shaped and it includes a first portion 20a that is adapted to mate to a vertebra, e.g., the inferior vertebra 60i, and a second portion 20b having the bearing element 22 disposed therein. The exemplary first and second portions 20a, 20b each have a substantially planar configuration, and each portion 20a, 20b can be positioned at an angle relative to one another. For example, the first and second portions 20a, 20b can be substantially perpendicular to one another. The configuration of each portion 20a, 20b relative to one another can, however, vary depending on the intended use.

As noted above, the first portion 20a is adapted to mate to a vertebra. While various techniques can be used to allow the first portion 20a to mate to a vertebra, in the illustrated exemplary embodiment the first portion 20a includes an opening 24 extending therethrough for receiving a portion of a fastening element and/or a bone engaging element. The opening 24 can vary in shape and size depending on the type of bone engaging element and fastening element being used. In an exemplary embodiment, as shown in FIG. 2B, the bone engaging element is a bone screw 50 and the fastening element is a locking nut 52 that is adapted to engage the bone screw 50 to lock the first portion 20a of the first element 20 relative to the vertebra 60i. In particular, the bone screw 50 has a threaded shank 50a that is adapted to extend into the vertebra 60i, a receiving head 50b formed on the threaded shank 50a, and a threaded central shaft 50c that extends from the receiving head 50b through the opening 24 in the first portion 20a and that mates to the locking nut 52. In one exemplary embodiment the receiving head 50b can have a shape that is configured to seat a posterior surface or articulating surface 26 of the first portion 20a of the first member 20 such that a position of the first member 20 relative to the bone screw 50 can be adjusted. For example, the receiving head 50b can include a substantially spherical recess 51 formed therein, and the articulating surface 26 of the first portion 20a of the first member 20 can be substantially spherical, as shown in FIG. 2A. As a result, the first member 20 can be angularly adjustable relative to the bone screw 50, and in particular relative to the vertebra 60i. Such a configuration allows the bearing element 22 of the second portion 20b of the first member 20 to be positioned as desired, as will be discussed in more detail below.

The second portion 20b of the first member 20 can also have a variety of configurations, but as noted above the exemplary second portion 20b includes a bearing element 22 disposed therein for receiving the extension rod 32 on the second member 30. Various bearing elements 22 known in the art can be used, but in the illustrated embodiment the bearing element 22 is a standard ball bearing that includes an opening 22i formed therethrough. The bearing element 22 can be disposed within the second portion 20b of the first member 20 using a variety of techniques, but in an exemplary embodiment the bearing element 22 is preferably freely rotatable relative to the second portion 20b of the first member 20. This will allow the bearing element 22 to pivot/rotate as the first and second members 20, 22 move relative to one another as a result of movement of the vertebrae 60s, 60i relative to one another. As shown in FIG. 2A, the bearing element 22 is disposed within a spherical recess 28 that is formed within and extends through an insert 27, and the insert 27 in turn is disposed within an opening 25 formed in the second portion 20b. A person skilled in the art will understand that the bearing element 22 can be directly disposed within a recess formed within the second portion 20b, and the use of an insert 27 is not necessary.

In order to facilitate free rotation/movement of the bearing element 22 within the recess 28, the bearing element 22 and/or the recess 28 can include a coating to reduce friction and reduce wear. The opening 22i in the bearing element 22 can also include a coating formed therein to reduce friction and wear on the bearing element 22 caused by movement of the extension rod 32 therethrough. Suitable exemplary materials for coating the bearing element 22, the recess 28, and/or the extension rod 32 include, by way of non-limiting example, titanium nitrite coating, titanium carbon-nitrite coating, diamond-like carbon coating, and other similar materials. The bearing element 22, the recess 28, and/or the extension rod 32, which will be discussed in more detail below, can also be formed from certain materials that are adapted to withstand wear, such as, for example, stainless steel, titanium, cobalt chrome, plastics such as polyethylene and polyurethane, and various ceramics.

Figure 3:
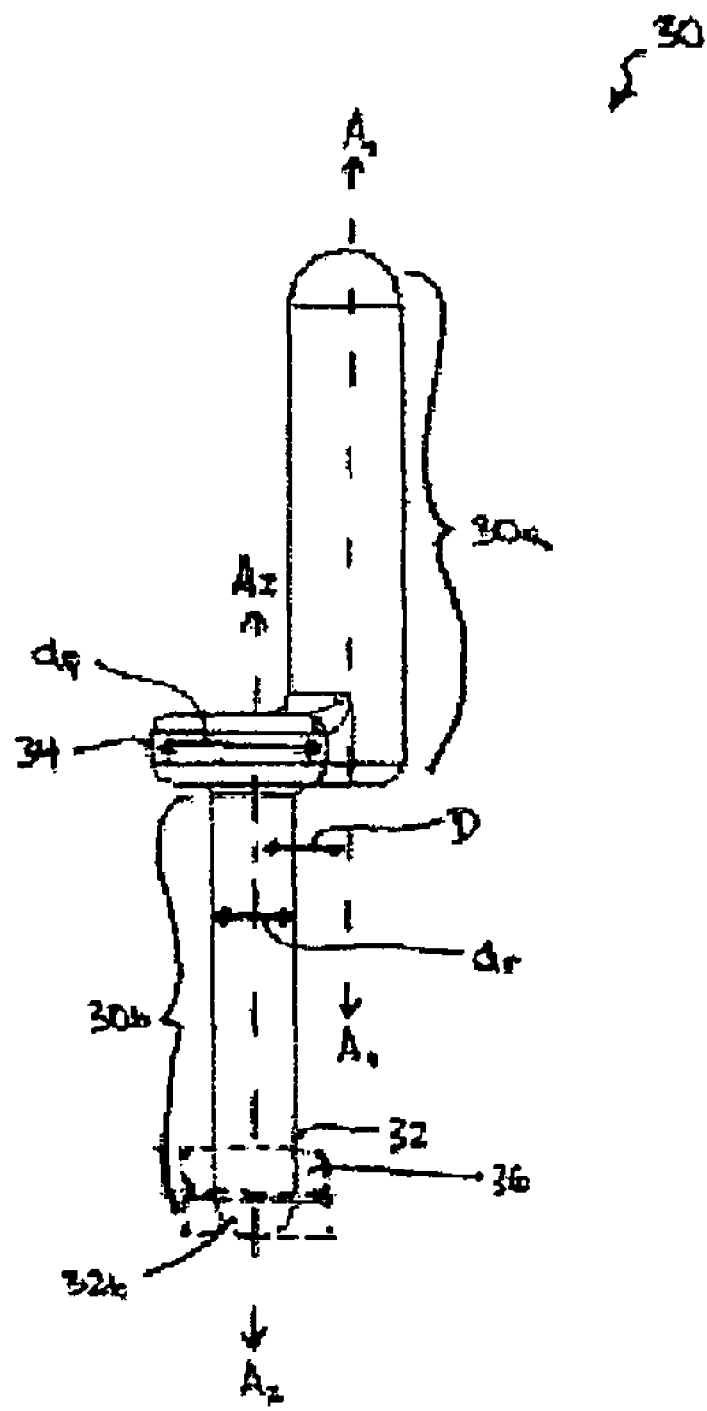
FIG. 3 is a side view of a second member of one of the exemplary implants shown in FIG. 1A.

The second member 30 of the implant 10 can also have a variety of configurations, but in one exemplary embodiment, as shown in more detail in FIG. 3, the second member 30 can have a substantially elongate shape with first and second portions 30a, 30b. The first portion 30a can be adapted to couple to a bone engaging element for mating the first portion 30a to a vertebra, e.g., the superior vertebra 60s, and the second portion 30b can form the extension rod 32 that is adapted to extend through the opening 22i formed in the bearing element 22. The first and second portions 30a, 30b can be coaxial with one another, but in an exemplary embodiment the first and second portions 30a, 30b are axially offset from one another. In particular, the axis $A_1$ of the first portion 30a can be spaced a distance D apart from the axis $A_2$ of the second portion 30b. While the distance can vary, in one exemplary embodiment the distance D can be in the range of about 2 mm to 10 mm. Such a configuration will facilitate positioning of the second portion 30b, e.g., the extension rod 32, relative to the bearing element 22, and it can also allow the extension rod 32 to move relative to the bearing element 22 without abutting against or otherwise coming into contact with the first portion 20a of the first member 20.

As noted above, the first portion 30a of the second member 30 can be adapted to couple to a bone engaging element to mate the first portion 30a to the superior vertebra 60s. Accordingly, the first portion 30a can have a variety of configurations depending on the type of bone engaging element used. In the exemplary embodiment shown in FIGS. 1A and 1B, the bone engaging element is a bone screw 54 having a shank (not shown) that threads into the vertebra 60s, and a U-shaped receiving head 56. Accordingly, the first portion 30a can be in the form of a rod that is adapted to seat within the receiving head 56. A locking element, such as a set screw, can be used to lock the first portion 30a within the receiving head 56, thereby mating the second member 30 to the vertebra 60s. In another exemplary embodiment, the bone screw 54 can be a polyaxial bone screw such that the receiving head 54 is angularly adjustable relative to the shank. Such a configuration will allow the second member 30 to be set at a desired position relative to the first member 20, and in particular the extension rod 32 can be positioned as desired relative to the bearing element 22. The orientation of the second member 30 relative to the first member 20 can be used to control movement of the vertebrae 60s, 60i relative to one another, as will be discussed in more detail below. A person skilled in the art will appreciate that a variety of other devices including, for example, offset connectors, can be used to mate the second member 30 to the vertebra.

The extension rod 32 of the second member 30 can also have a variety of configurations, but it should be adapted to be extend through and slidably move relative to the bearing element 22. In the illustrated exemplary embodiment, the extension rod 32 has a substantially cylindrical shape with a diameter $d_r$ that is only slightly less than an inner diameter $d_i$ of the opening formed through the bearing element 22.

The extension rod 32 can also include one or more physical stops formed thereon to limit movement thereof relative to the bearing element 22. While the physical stop(s) can have a variety of shapes and sizes, in the illustrated exemplary embodiment the first portion 30a and the extension rod 32 are separated by a substantially circular flange 34 that forms a physical stop. The flange 34 can be adapted to abut against a superior surface 20s (FIG. 2A) of the first member 20 to limit penetration of the extension rod 32 through the bearing element 22. Accordingly, the flange 34 preferably has an extent, e.g., a diameter $d_f$, that is larger than the diameter $d_i$ of the opening 22i in the bearing element. The terminal end 32t of the extension rod 32 can also include a flange formed thereon, as is further shown in FIG. 3, to prevent removal of the extension rod 32 from the bearing element 22.

The extension rod 32 can also include one or more compressive elements disposed there around and adapted to act as a cushion for preventing hard contact between the extension rod 32 and the bearing element 22, or the second portion 20b of the first member 20. As shown in FIG. 3, the compressive element 36 can be in the form of a donut or similar shaped member that is disposed around the extension rod 32. The compressive element 36 can be positioned adjacent to the flange 34, or it can be disposed or formed on the terminal end 32t of the extension rod 32 as shown. Alternatively, the flange on the terminal end 32t can be formed from a compressive material, or it can include a compressive element mated thereto or formed thereon. A person skilled in the art will appreciate that a variety of techniques can be used to control movement of and limit hard impact between the extension rod 32 and the bearing element 22. A person skilled in the art will also appreciate that a variety of materials can be used to form a compressive element. By way of non-limiting example, suitable materials include polymers, such as polyurethane, silicone-urethane copolymer, polycarbonateurethane. Metallic springs can also be used.

In use, the implant 10 can replace and/or augment one or more of the posterior elements of the spine, including, for example, the facet joints, the lamina, the posterior ligaments, and/or other features of a patient's spinal column. The particular configuration and use of the implant 100 can, however, vary depending on the specific procedure being performed. For example, where a laminectomy is performed and the facet joints are not removed, the implant can be used to reduce the load on the facet joints. Where the facet joints are removed, it may be necessary to add an anti-rotation feature, as will be discussed in more detail below, to prevent rotation of the bone screws relative to the vertebrae. Where the posterior ligaments are removed, it may be desirable to use one or more compressive elements to facilitate control of flexion of the vertebrae. The implant 10 can also be adapted to function with either a natural vertebral disc, or with an artificial disc as previously discussed. Regardless, as noted above, the implant 10 is preferably adapted to allow flexion, extension, and lateral bending of the spine, while substantially restricting posterior-anterior shear and rotation of the spine. While an exemplary method of implanting only one posterior stabilizing implant 10 will be discussed, a person skilled in the art will appreciate that, in an exemplary embodiment, two implants 10, 10' are implanted on opposed lateral sides of adjacent vertebrae. Moreover, any number of implants can be used to couple multiple adjacent vertebrae depending on the needs of the patient.

One exemplary procedure can begin by implanting a bone screw 50 in the inferior vertebra 60i, and implanting a bone screw 54 in the superior vertebra 60s. As shown in FIGS. 1A and 1B, the bone screws 50, 54 are implanted on a lateral side of the vertebrae 60s, 60i to allow another implant 10' to be implanted on the opposed lateral side of the vertebrae 60s, 60i. Once the bone screws 50, 54 are implanted, the first member 20 can be coupled to bone screw 50 by positioning the articulating surface 26 of the first portion 20a on the receiving head such that the central shaft of the bone screw 50 extends through the opening 24 in the first member 20. The locking nut 52 can then be loosely threaded onto the central shaft of the bone screw 50 to loosely attach the first member 20 to the bone screw 50. The first member 20 can then be angularly adjusted as desired, and once properly positioning, the locking nut 52 can be tightened to maintain the first member 20 in a fixed position relative to the vertebra 60i. The second member 30 can be coupled to bone screw 54 by inserting the extension rod 32 through the bearing element 22 and positioning the first portion 30a within the receiving head 56 of the bone screw 54. The locking element, e.g., set screw 58, can then be inserted into the receiving head 56 to loosely mate the second member 30 to the vertebra 60s. Where the bone screw 54 is a polyaxial bone screw, the second member 30 can be angularly adjusted by moving the receiving head 56. Once the second member 30 is properly positioned, the set screw 58 can be fully tightened to maintain the second member 30 in a fixed position relative to the vertebra 60s. A person skilled in the art will appreciate that the bone screws 50, 54 and the first and second members 20, 30 can be implanted and adjusted in any order. In one exemplary embodiment, the second member 30 is positioned as desired and the first member 20 is then positioned as necessary based on the positioning of the second member 30.

While not shown, where the implant 10 is used to replace the facet joints, it may be desirable to include an anti-rotation feature to prevent rotation of the bone screws that are implanted in the superior vertebra 60s. While various anti-rotation techniques can be used, in one embodiment the bone screws can include spikes or other surface protrusions formed on a proximal end of the shank or on the head of the screws to prevent rotation thereof. In another embodiment, a cross-connector can be connected to and extend between the first portion of the second member of each implant, thereby preventing rotation of the bone screw mated thereto.

Once the implant 10 is coupled to the adjacent vertebrae 60s, 60i, the implant 10 can control movement of the vertebrae 60s, 60i relative to one another. In particular, during movement of the spine, the bearing element 22 rotates as the extension rod 32 slidably moves therethrough to control movement of the vertebrae 60s, 60i. Due to the configuration of the implant 10, the bearing element 22 and the extension rod 32 can also substantially prevent axial rotation of the vertebrae 60s, 60i relative to one another, and anterior-posterior shearing can be substantially resisted. FIGS. 4A-4C illustrate the vertebrae 60s, 60i in a neutral position, and during flexion and extension. FIG. 4A illustrates the vertebrae 60s, 60i in a neutral position, 60i. FIG. 4B illustrates the vertebrae 60s, 60i during extension, and as shown the extension rod 32 is fully inserted into the bearing element 22 such that the flange 34 abuts against the bearing element 22. FIG. 4C illustrates flexion of the vertebrae 60s, 60i, and as shown the bearing element 22 is pivoted relative to the first member 20 and the extension rod 32 is substantially withdrawn from the bearing element 22 such that only the terminal end 32t of the extension rod 32 remains in the bearing element 22.

While the extension rod 32 can be positioned to be substantially parallel to the central axis X of the vertebrae 60s, 60i, the extension rod 32 can be positioned at a particular angle relative to the central axis X of the vertebrae 60s, 60i to control the movement of the vertebrae 60s, 60i. As shown in FIG. 4A, the position of the extension rod 32 relative to the vertebrae 60s, 60i is indicated by angle α, which is measured between a line perpendicular to the central axis X and the axis $A_2$ of the extension rod 32. In order to increase flexion, the extension rod 32 can angled toward the central axis of the vertebrae 60s, 60i such that the angle α is less than 90°. At this angle, the flange 34 will be positioned closer to the bearing element 22 in the neutral position. As a result, when the vertebrae 60s, 60i move from the neutral position, shown in FIG. 4A, to the extended position, shown in FIG. 4B, the range of motion will be limited. Conversely, when the vertebrae 60s, 60i move from the neutral position to the flexed position, shown in FIG. 4C, the range of motion will be greater. In order to decrease flexion, the extension rod 32 can angled away from the central axis of the vertebrae 60s, 60i such that the angle α is greater than 90°. At this angle, the flange 34 will be spaced a greater distance apart from the bearing element 22 in the neutral position. As a result, when the vertebrae 60s, 60i move from the neutral position, shown in FIG. 4A, to the extended position, shown in FIG. 4B, the range of motion will be increased. Conversely, when the vertebrae 60s, 60i move from the neutral position to the flexed position, shown in FIG. 4C, the range of motion will be decreased. Accordingly, the angle α of the extension rod 32 can be selected based on the desired range of motion during flexion and extension. A person skilled in the art will appreciate that the angle α can vary depending on the desired result, but in an exemplary embodiment the angle α can be in the range of about 60° to about 120°.

While not shown, the procedure can also include the step of placing a sheath or protective member partially or fully around the implant 10 for preventing tissue from growing on the implant 10 and into the bearing element 22, and for preventing debris from migrating into the spinal canal.

FIGS. 5A-8C illustrate another exemplary embodiment of a posterior stabilizing implant 10. The implant 100 is somewhat similar to implant 10, except that it has a bilateral configuration. In particular, rather than having two implants 10, 10' positioned on opposed lateral sides of two adjacent vertebrae, implant 100 can be positioned along the mid-line of the adjacent vertebrae to control movement of the vertebrae relative to one another.

Figure 5A:
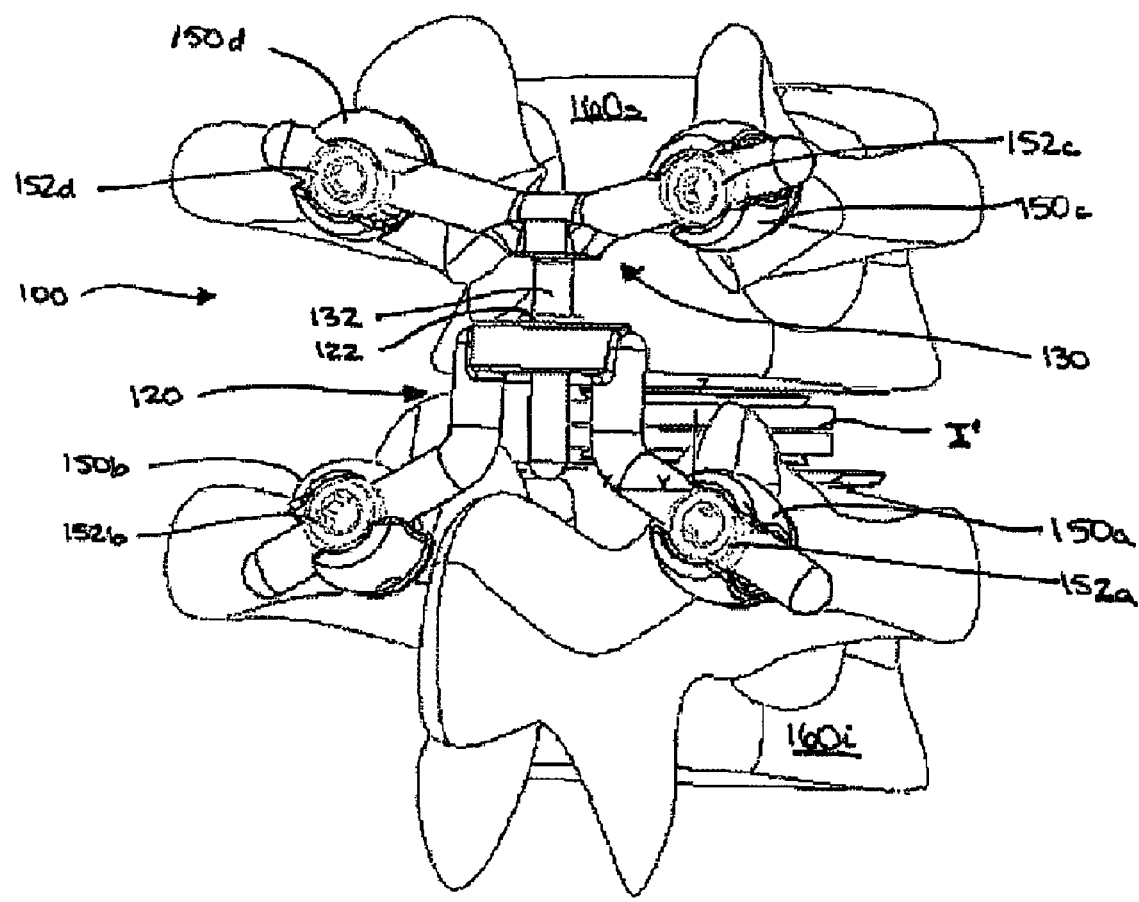
FIG. 5A is a perspective view of another exemplary embodiment of a posterior stabilizing implant coupled to adjacent vertebrae.
Figure 5B:
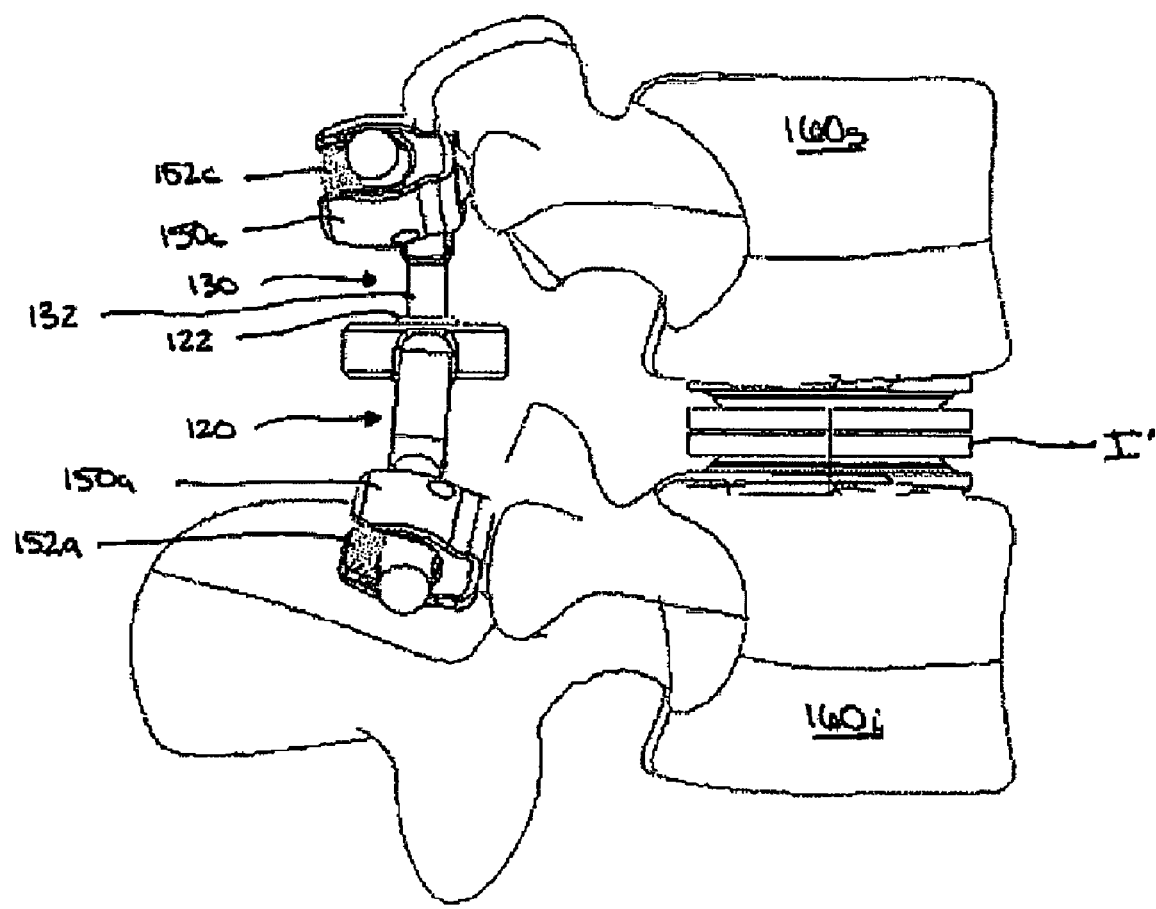
FIG. 5B is a side view of the posterior stabilizing implant shown in FIG. 5A.

As shown in FIGS. 5A and 5B, the exemplary implant 100 generally includes a first member 120 that is adapted to couple to a first vertebra, e.g., an inferior vertebrae 160i, and that includes a bearing element 122 disposed therein, and a second member 130 that is adapted to couple to a second vertebrae, e.g., a superior vertebrae 160s, and that has an extension rod 132 formed thereon. While not shown, the first and second members 120, 130 can be reversed such that the first member 120 is coupled to the superior vertebra 160s and the second member 130 is coupled to the inferior vertebra 160i. In use, the bearing element 122 is adapted to freely rotate relative to the first member 120, and the extension rod 132 is adapted to slidably extend through the bearing element 122 to control movement of the adjacent vertebrae 160s, 160i, allowing flexion, extension, and lateral bending of the spine, while substantially restricting posterior-anterior shear and rotation of the spine. While not shown, the first and second members 120, 130 can be reversed such that the first member 20 is coupled to the superior vertebra 60s and the second member 30 is coupled to the inferior vertebra 60i.

Figure 6:
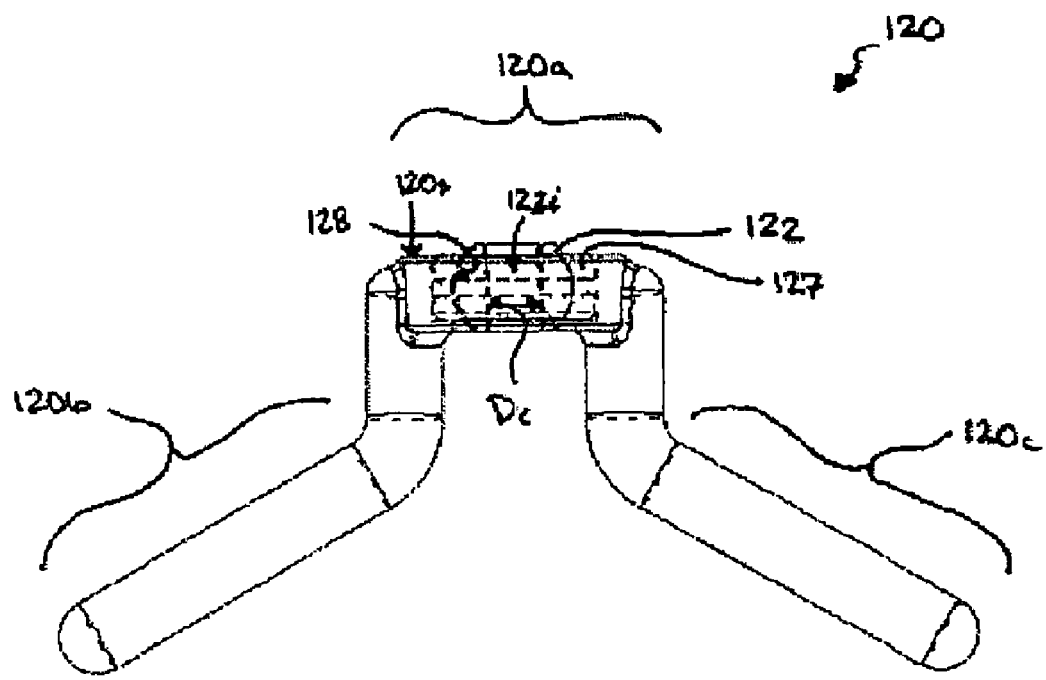
FIG. 6 is a side view of a first member of the exemplary implant shown in FIG. 5A.

The first member 120 of the implant 100, which is shown in more detail in FIG. 6, can have a variety of configurations. In the illustrated exemplary embodiment, however, the first member 120 is substantially Y-shaped and it includes a central portion 120a having the bearing element 122 disposed therein, and first and second arms 120b, 120c that extend from the central portion 120a and that are adapted to mate to a vertebra, e.g., the inferior vertebra 60i. The central portion 120a and the first and second arms 120b, 120c can have a variety of shapes and sizes, and the configuration can vary depending on the intended use. In the illustrated exemplary embodiment, the central portion 120a has a substantially planar cylindrical configuration such that it is adapted to seat the bearing element 122 therein, and the first and second arms 120b, 120c each extend distally and laterally outward from the central portion 120a. Such a configuration allows the first and second arms 120b, 120c to mate to opposed lateral sides of the vertebra 160i.

The first and second arms 120b, 120c can mate to the inferior vertebra 160i using a variety of techniques. In the illustrated exemplary embodiment, the arms 120b, 120c are in the form of rods having a generally elongate, substantially cylindrical configuration. This allows each arm 120b, 120c to be received within a receiving head of a bone engaging element. In the embodiment shown in FIGS. 5A and 5B, the bone engaging elements are bone screws 150a, 150b that are implanted on opposed lateral sides of the inferior vertebra 160i. As previously described above with respect to FIGS. 1A and 1B, the bone screws 150a, 150b can include a U-shaped head that is adapted to seat an arm 120b, 120c, and a locking element, such as a set screw 152a, 152b can be used to lock the arms 120b, 120c to the bone screws 150a, 150b. The receiving head of each bone screw 150a, 150b can also be polyaxially movable relative to the threaded shank (not shown) of the bone screw 150a, 150b to allow the first member 120 to be angularly adjustable relative to the vertebra 160i. Such a configuration allows the bearing element 122 to be positioned as desired, as will be discussed in more detail below.

As noted above, the first member 120 also includes a bearing element 122 disposed therein. The bearing element 122 can have a configuration that is the same as or similar to the configuration previously described with respect to bearing element 22 shown in FIGS. 1A-2. In particular, the bearing element 122 can be freely rotatably disposed within a spherical recess formed in the central portion 120a of the first member 120, or it can be freely rotatably disposed within an insert 127 that is disposed within the central portion 120a of the first member 120, as shown in FIG. 6. As was also previously described, the bearing element 122 can be a standard ball bearing that includes an opening 122i formed therethrough for slidably receiving the extension rod 132 on the second member 130. The bearing element 122, the recess 128 formed within the insert 127 for seating the bearing element 122, and/or the opening 122i formed through the bearing element 122 can also include a coating to reduce friction and reduce wear.

Figure 7:
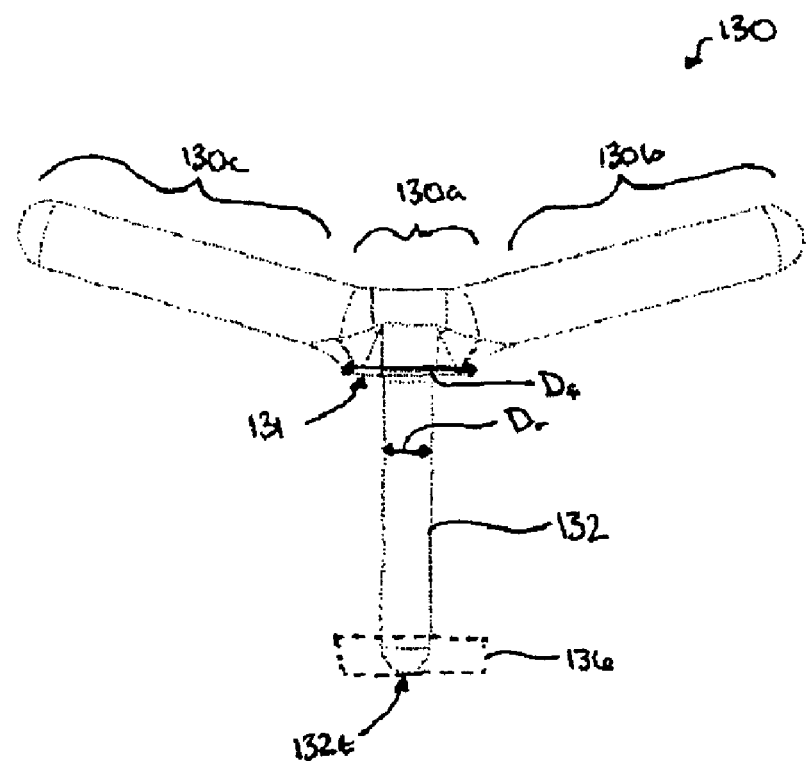
FIG. 7 is a side view of a second member of the exemplary implant shown in FIG. 5A.

The second member 130 of the implant 10 can also have a variety of configurations, but in an exemplary embodiment, as shown in more detail in FIG. 7, the second member 130 can be substantially Y-shaped with a central portion 130a having first and second arms 130b, 130c extending laterally from opposed sides thereof. The extension rod 132 can also extend from the central portion 130a. The particular angle of each arms 130b, 130c relative to the extension rod 132 can vary depending on the intended use, but in an exemplary embodiment 130b, 130c that arms have a configuration that allows each arm 130b, 130c to mate to opposed lateral sides of a vertebra, e.g., the superior vertebra 160s.

Each arm 130b, 130c can be mated to the vertebra 160s using a variety of techniques, however in an exemplary embodiment each arm 130b, 130c is in the form of a rod having a substantially elongate cylindrical shape such that the arms 130b, 130c can mate to a receiving head of a bone engaging element, such as bone screws 150c and 150d as shown. As previously described, the bone screws 150c, 150d can be polyaxial bone screws to allow the position of the second member 130 to be angularly adjusted as desired, and in particular to allow the extension rod 132 to be positioned as desired relative to the bearing element 122. A locking element, such as a set screw 152c, 152d can be used to lock the arms 130b, 130c to the bone screws 150c, 150d.

The extension rod 132 of the second member 130 can also have a variety of configurations, but in an exemplary embodiment the extension rod 132 is similar to extension rod 22 previously described with respect to FIGS. 1A, 1B, and 3. In particular, the extension rod 132 should be adapted to extend through and slidably move relative to the bearing element 122. In the illustrated exemplary embodiment, the extension rod 32 has a substantially cylindrical shape with a diameter $D_r$ that is only slightly less than an inner diameter $D_i$ of the opening formed through the bearing element 122.

As previously described with respect to FIG. 3, the extension rod 132 can also include a physical stop formed thereon to limit movement thereof relative to the bearing element 122. While the physical stop can have a variety of shapes and sizes, in the illustrated exemplary embodiment the central portion 130a has a substantially cylindrical shape with a surface 131 that is adapted to abut against the bearing element 122 to limit penetration of the extension rod 132 through the bearing element 122. Accordingly, the surface 131 preferably has an extent, e.g., a diameter $D_f$, that is larger than the diameter $D_i$ of the opening 122i in the bearing element.

The extension rod 132 can also include one or more compressive elements disposed there around, as previously described with respect to FIG. 3, for providing a cushion to substantially prevent hard contact between the extension rod 132 and the bearing element 122, or the central portion 120a of the first member 120. The compressive element(s) (not shown) can be in the form of a donut or similar shaped member that is disposed around the extension rod 132. The compressive element can be positioned adjacent to surface 131, and/or it can be disposed or formed on the terminal end 132t of the extension rod 32. The terminal end 132t can also include a stop surface or flange 136 formed thereon, as shown in phantom in FIG. 7, to prevent the extension rod 132 from being fully withdrawn from the bearing element 122, and optionally to retain a compressive element on the extension rod 132. Alternatively, flange 136 can be formed from a compressive material, or it can include a compressive element mated thereto or formed thereon. A person skilled in the art will appreciate that a variety of techniques can be used to control movement of and limit hard impact between the extension rod 132 and the bearing element 122. A person skilled in the art will also appreciate that a variety of materials can be used to form a compressive element.

While not shown, in another exemplary embodiment the extension rod 132 can be adjustable relative to the first and second arms 130b, 130c. For example, the extension rod 132 can be rotatably mated to the central portion 130a, and the central portion 130a can include a locking mechanism that is adapted to lock the extension rod 132 in a desired fixed position. Such a configuration is particularly desirable where the bone screws 150c, 150d used to attach the arms 130b, 130c to the vertebra 160s are not polyaxial. The extension rod 132 can thus be positioned at a desired angle relative to the vertebra 160s, and then locked in place to maintain it at the desired angular position. A person skilled in the art will appreciate that a variety of other techniques can be used to allow the extension rod 132 to be adjusted relative to the remainder of the second member 130.

In use, the implant 100 can replace and/or augment one or more of the posterior elements of the spine, including, for example, the facet joints, the lamina, the posterior ligaments, and/or other features of a patient's spinal column. The implant 100 can also be adapted to function with either a natural vertebral disc, or with an artificial disc as previously discussed. Regardless, as noted above, the implant 100 is preferably adapted to allow flexion, extension, and lateral bending of the spine, while substantially restricting posterior-anterior shear and rotation of the spine. The particular configuration and use of the implant 100 can, however, vary depending on the specific procedure being performed. For example, where a laminectomy is performed and the facet joints are not removed, the implant can be used to reduce the load on the facet joints. Where the facet joints are removed, it may be necessary to add an anti-rotation feature as previously discussed to prevent rotation of the bone screws relative to the vertebrae. Where the posterior ligaments are removed, it may be desirable to use one or more compressive elements to facilitate control of flexion of the vertebrae.

One exemplary procedure can begin by implanting two bone screws 150a, 150b in the inferior vertebra 160i, and implanting two bone screws 150c, 150d in the superior vertebra 160s. As shown in FIGS. 5A and 5B, the bone screws 150a, 150b, 150c, 150d are implanted on opposed lateral sides of the vertebrae 160s, 160i. Once the bone screws 150a, 150b, 150c, 150d are implanted, the first member 120 can be coupled to bone screws 150a, 150b by positioning the arms 120b, 120c in the receiving head of the bone screws 150a, 150b such that the central portion 120a is positioned toward the superior vertebra 160s. The set screws 152a, 152b can then be loosely threaded onto the receiving heads of the bone screws 150a, 150b to loosely attach the first member 120 to the bone screws 150a, 150b. Where the bone screws 150a, 150b are polyaxial bone screws, the first member 120 can be angularly adjusted by moving the receiving heads of the screws 150a, 150b. Once properly positioned, the set screws 152a, 150s can be tightened to maintain the first member 120 in a fixed position relative to the vertebra 160i. As previously described, the extension rod 132 can be positioned at a desired angle relative to the vertebrae 160s, 160i. The second member 130 can similarly be coupled to two bone screws 150c, 150d by inserting the extension rod 132 through the bearing element 122, and positioning the arms 130b, 130c within the receiving heads of the bone screws 150c, 150d. The set screws 152c, 152d can be loosely mated to the receiving heads to retain the arms 130b, 130c therein. Where the bone screws 150c, 150d are polyaxial bone screws, the second member 130 can be angularly adjusted by moving the receiving heads of the screws 150c, 150d. Once the second member 130 is properly positioned, the set screws 152c, 152d can be fully tightened to maintain the second member 130 in a fixed position relative to the vertebra 160s. A person skilled in the art will appreciate that the bone screws 150a, 150b, 150c, 150d and the first and second members 120, 130 can be implanted and adjusted in any order. In one exemplary embodiment, the second member 130 is positioned as desired and the first member 120 is then positioned as necessary based on the positioning of the second member 130.

Once the implant 100 is coupled to the adjacent vertebrae 160s, 160i, the implant 100 can control movement of the vertebrae 160s, 160i relative to one another. In particular, during movement of the spine, the bearing element 122 rotates as the extension rod 132 slidably moves therethrough to control movement of the vertebrae 160s, 160i. Due to the configuration of the implant 100, the bearing element 122 and the extension rod 132 can also substantially prevent axial rotation of the vertebrae 160s, 160i relative to one another, and anterior-posterior shearing can be substantially resisted. FIGS. 8A-8C illustrate the vertebrae 160s, 160i in a neutral position, and during flexion and extension. FIG. 8A illustrates the vertebrae 160s, 160i in a neutral position, and as shown the extension rod 132 is substantially parallel to the central axis Y of the vertebrae 160s, 160i. FIG. 8B illustrates the vertebrae 160s, 160i during extension, and as shown the extension rod 132 is fully inserted into the bearing element 122 such that surface 131 abuts against the bearing element 122. FIG. 8C illustrates flexion of the vertebrae 160s, 160i, and as shown the bearing element 122 is pivoted relative to the first member 120 and the extension rod 132 is substantially withdrawn from the bearing element 122 such that only the terminal end 132t of the extension rod 132 remains in the bearing element 122.

While not shown, the procedure can also include the step of placing a sheath or protective member partially or fully around the implant 100 for preventing tissue from growing on the implant 100 and into the bearing element 122, and for preventing debris from migrating into the spinal canal.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method for stabilizing the posterior element in adjacent vertebrae, comprising:
coupling a first portion of a first member to a first vertebra and a second member to a second vertebra such that an extension rod on the second member extends through a bearing element disposed within a second portion of the first member and such that the extension rod extends out of opposite ends of the second portion, the bearing element being rotatably disposed within the first member to thereby allow flexion, extension, and lateral bending of the first and second vertebrae relative to one another, the extension rod sliding freely through the bearing element during movement of the first and second vertebrae, and the second member including a stop formed thereon for limiting movement of the second member relative to the bearing element;
wherein the first member is coupled to the first vertebra by implanting a bone engaging member in the first vertebra and mating the first portion of the first member to the bone engaging member, and wherein the second member is coupled to the second vertebra by implanting a bone engaging member in the second vertebra and mating a portion of the second member to the bone engaging member; and
wherein the first member is substantially L-shaped with the first portion being adapted to mate to the bone engaging element, and the second portion having the bearing element rotatably disposed therein, and the second member comprises a substantially elongate member having a first portion that is adapted to mate to the bone engaging element and a second portion that is adapted to be disposed through the bearing element.

2. The method of claim 1, further comprising positioning the extension rod at a predetermined angle relative to a central axis of the first and second vertebrae.

3. The method of claim 2, wherein the angle is in the range of about 60° to about 120°.

4. The method of claim 1, wherein the stop is formed on the second member between the first and second portions, the stop being adapted to limit movement of the second portion relative to the bearing element.

5. The method of claim 1, wherein the first and second portions of the second member are axially offset from one another.

6. A method for stabilizing the posterior element in adjacent vertebrae, comprising:
implanting a first bone engaging member in a first vertebra;
coupling a first member to the first bone engaging member;
implanting a second bone engaging member in a second vertebra;
coupling a first extension rod of a second member to the second bone engaging member; and
positioning a second extension rod axially offset from the first extension rod of the second member through a bearing element such that the second portion of the second member extends out of opposite ends of the bearing element, the bearing element being rotatably disposed within the first member to allow movement of the first and second vertebrae relative to one another, and the first and second extension rods extending from a stop disposed therebetween that limits slidable movement of the second extension rod through the bearing element.

7. The method of claim 6, wherein the first and second members allow flexion, extension, and lateral bending of the first and second vertebra relative to one another.

8. The method of claim 7, wherein the first and second members substantially restrict posterior-anterior shear and rotation of the first and second vertebra relative to one another.

9. The method of claim 6, wherein the second portion of the second member slides freely through the bearing element during movement of the first and second vertebrae.

* * * * *